United States Patent
Deal et al.

(10) Patent No.: US 10,365,192 B2
(45) Date of Patent: Jul. 30, 2019

(54) APPARATUS AND METHOD FOR RAPID SCREENING OF MATERIAL PROPERTIES IN A PLURALITY OF ADDITIVELY MANUFACTURED TEST SPECIMENS

(71) Applicant: General Electric Company, Schenectady, NY (US)

(72) Inventors: Andrew David Deal, Niskayuna, NY (US); Timothy Hanlon, Glenmont, NY (US); Vipul Kumar Gupta, Guilderland, NY (US); Erica Elizabeth Sampson, Clifton Park, NY (US); Justin John Gambone, Jr., Watervliet, NY (US); Scott Michael Oppenheimer, Schenectady, NY (US); Laura Cerully Dial, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 275 days.

(21) Appl. No.: 15/397,520

(22) Filed: Jan. 3, 2017

(65) Prior Publication Data
US 2018/0188144 A1    Jul. 5, 2018

(51) Int. Cl.
*G01N 3/10*    (2006.01)
*G01N 3/18*    (2006.01)
(Continued)

(52) U.S. Cl.
CPC ............. *G01N 3/10* (2013.01); *B29C 64/386* (2017.08); *B33Y 40/00* (2014.12); *B33Y 50/00* (2014.12);
(Continued)

(58) Field of Classification Search
CPC .. G01N 3/10; G01N 3/32; G01N 3/08; G01N 3/18; B29C 64/386; B33Y 40/00; B33Y 50/00
(Continued)

(56) References Cited

U.S. PATENT DOCUMENTS 9,109,979 B2    8/2015  Dietrich et al.
2009/0326706 A1*  12/2009  Fink .................... B29C 64/153
                                            700/212
(Continued)

FOREIGN PATENT DOCUMENTS

CN    107389447 A    11/2017
WO    2015148208 A1  10/2015

OTHER PUBLICATIONS

Triantaphyllou et al., "Surface Texture Measurement for Additive Manufacture", Spring Topical Meeting, vol. 47, pp. 127-130, http://aspe.net/publications/spring_2014/2014 aspe spring proceedings-print final.pdf, 2014.
(Continued)

*Primary Examiner* — Nathaniel T Woodward
(74) *Attorney, Agent, or Firm* — Jennifer Ward

(57) ABSTRACT

An apparatus and method for rapid screening of material properties in a plurality of additively manufactured test specimens. The apparatus includes a build plate having the plurality of additively manufactured test specimens disposed on a first substantially planar surface. The plurality of additively manufactured test specimens are coupled to at least one actuator to one of individually or simultaneously translationally displace each of the test specimens along an axis "z", and perpendicular to the build plane of the build plate to test material properties of each of the plurality of additively manufactured test specimens. A sensor is coupled to each of the plurality of additively manufactured test specimens. Load vs. displacement data may be used to
(Continued)

monitor the progression of monotonic and/or cyclic tests of the plurality of additively manufactured test specimens.

27 Claims, 5 Drawing Sheets

(51) Int. Cl.
  *B33Y 40/00* (2015.01)
  *B33Y 50/00* (2015.01)
  *G01N 3/08* (2006.01)
  *G01N 3/32* (2006.01)
  *B29C 64/386* (2017.01)
(52) U.S. Cl.
  CPC ............... *G01N 3/08* (2013.01); *G01N 3/18* (2013.01); *G01N 3/32* (2013.01)
(58) Field of Classification Search
  USPC .......................................... 73/819
  See application file for complete search history.

(56) References Cited

U.S. PATENT DOCUMENTS

| | | | |
|---|---|---|---|
| 2011/0121492 A1* | 5/2011 | Philippi | G01N 29/12 264/401 |
| 2011/0137578 A1* | 6/2011 | Dietrich | G01N 3/08 702/43 |
| 2013/0316081 A1* | 11/2013 | Kovalcik | B22F 3/1055 427/265 |
| 2014/0163717 A1 | 6/2014 | Das et al. | |
| 2015/0056464 A1 | 2/2015 | Brice | |
| 2016/0169821 A1 | 6/2016 | Meyer et al. | |
| 2016/0199911 A1 | 7/2016 | Dave et al. | |
| 2016/0258852 A1 | 9/2016 | Bellemare et al. | |
| 2017/0138906 A1* | 5/2017 | Hartwig | G01M 7/022 |
| 2017/0190120 A1* | 7/2017 | Bloome | B33Y 30/00 |

OTHER PUBLICATIONS

Forster, "Materials Testing Standards for Additive Manufacturing of Polymer Materials: State of the Art and Standards Applicability", National Institute of Standards and Technology, pp. 10 of 54, http://nvlpubs.nist.gov/nistpubs/r/2015/NIST.IR.8059.pdf, May 2015.
Chen et al., "Design and Fabrication of a Bistable Unit Actuator with Multi-material Additive Manufacturing", SFF technical Program, pp. 21 of 52, http://sffsymposium.engr.utexas.edu/sites/default/files/2016/SFF Technical Program Final July 25.pdf, Aug. 8, 2016.
International Search Report and Written Opinion issued in connection with corresponding PCT Application No. PCT/US17/66055 dated Mar. 14, 2018.

* cited by examiner

APPARATUS AND METHOD FOR RAPID SCREENING OF MATERIAL PROPERTIES IN A PLURALITY OF ADDITIVELY MANUFACTURED TEST SPECIMENS

BACKGROUND

The present invention relates generally to material development of additively manufactured components, and more particularly to an apparatus and method for rapid screening of material properties in a plurality of additively manufactured test specimens.

There exists a wide array of available techniques for forming components. Components may be formed from molding, machining, and the like. Molding relies upon a liquid material to be poured or injected into a mold. The liquid material solidifies forming a component. The component may be further finished if so desired. Machining is a subtractive manufacturing process that employs cutters and the like to remove material from a substrate to form a component. Another process currently in use is additive manufacturing (AM) or 3-D printing. In additive manufacturing, a component is formed one layer of material at a time. More specifically, in powder-bed additive manufacturing, a layer of powder material is deposited onto a substrate, and melted through exposure to heat, a laser, an electron beam or some other process and subsequently solidified. Once solidified, a new layer is deposited, solidified, and fused to the previous layer until the component is formed.

In an attempt to optimize materials development for AM specific applications, materials property screening during the process optimization is required. Current mechanical testing for this type of processed material can take months to years. This translates into significant monetary, infrastructure, and personnel expenditures. Traditional processing methods (e.g. casting, and deformation processing) are more established with fewer variables, and the effects of such variables on material properties are more predictable. AM process variables, on the other hand, are highly linked to material performance, with unknown transfer functions in many cases. Therefore, it is imperative that design, process optimization, and material optimization (chemistry/post-processing treatments) are enabled in parallel.

Accordingly, there is a desire to incorporate material property screening into a standard methodology for processing optimization. More specifically, a screening apparatus and method is desired that provides rapid screening of relevant monotonic and cyclic mechanical properties of additively built specimens.

BRIEF DESCRIPTION

These and other shortcomings of the prior art are addressed by the present disclosure, which includes an apparatus and method for rapid screening of material properties in a plurality of additively manufactured test specimens.

According to one aspect of an exemplary embodiment, an apparatus for rapid screening of material properties in a plurality of additively manufactured test specimens is provided. The apparatus comprising a build plate, at least one actuator and a plurality of sensors. The build plate having a body, a first substantially planar surface and an opposing second substantially planar surface. The first substantially planar surface defining a build plane. The plurality of additively manufactured test specimens disposed on the first substantially planar surface. The at least one actuator, translationally displacing at least one of the plurality of additively manufactured test specimens along an axis to test material properties of at least one of the plurality of additively manufactured test specimens. At least one of the plurality of sensors is coupled to a respective one of the plurality of additively manufactured test specimens.

According to another aspect of an exemplary embodiment, an apparatus for rapid screening of material properties in a plurality of additively manufactured test specimens is provided. The apparatus comprising a build plate having a body, a first substantially planar surface and an opposing substantially planar second surface, the first substantially planar surface defining a build plane. The plurality of additively manufactured test specimens disposed on the first substantially planar surface. The plurality of additively manufactured test specimens are formed through a selective laser melting process and wherein each of the plurality of additively manufactured test specimens is coupled to the build plate in a manner that provides for a cross-sectional area "a" of each of the plurality of additively manufactured test specimens disposed proximate the build plate, to be greater than a cross-sectional area "b" of a centralized portion of the additively manufactured test specimens, and wherein the cross-sectional area "a" is greater than cross-sectional area "b". The apparatus further including at least one actuator and a plurality of sensors. Each of the at least one actuator translationally displacing at least one of the plurality of additively manufactured test specimens along an axis "z", and perpendicular to the build plane of the build plate to test material properties of at least one of the plurality of additively manufactured test specimens. At least one of the plurality of sensors is coupled to a respective one of the plurality of additively manufactured test specimens.

According to yet another aspect a method of for rapid screening of material properties in a plurality of additively manufactured test specimens is provided. The method comprising providing a build plate having a body, a first substantially planar surface and an opposing substantially planar second surface, the first substantially planar surface defining a build plane. The method further comprising covering portions of the first substantially planar surface of the build plate with an additively manufactured medium in successive layers to form the plurality of additively manufactured test specimens. At least one actuator is next to a support plate having disposed thereon a plurality of sensors coupled to each of the plurality of additively manufactured test specimens. The method further comprising actuating the at least one actuator to translationally displace at least one of the plurality of additively manufactured test specimens along an axis to test material properties of each of the plurality of additively manufactured test specimens.

Various refinements of the features noted above exist in relation to the various aspects of the present disclosure. Further features may also be incorporated in these various aspects as well. These refinements and additional features may exist individually or in any combination. For instance, various features discussed below in relation to one or more of the illustrated embodiments may be incorporated into any of the above-described aspects of the present disclosure alone or in any combination. Again, the brief summary presented above is intended only to familiarize the reader with certain aspects and contexts of the present disclosure without limitation to the claimed subject matter.

BRIEF DESCRIPTION OF DRAWINGS

The subject matter of this disclosure is particularly pointed out and distinctly claimed in the claims at the conclusion of the specification. The foregoing and other features, and advantages of the disclosure are apparent from the following detailed description taken in conjunction with the accompanying drawings in which:

Figure 1:
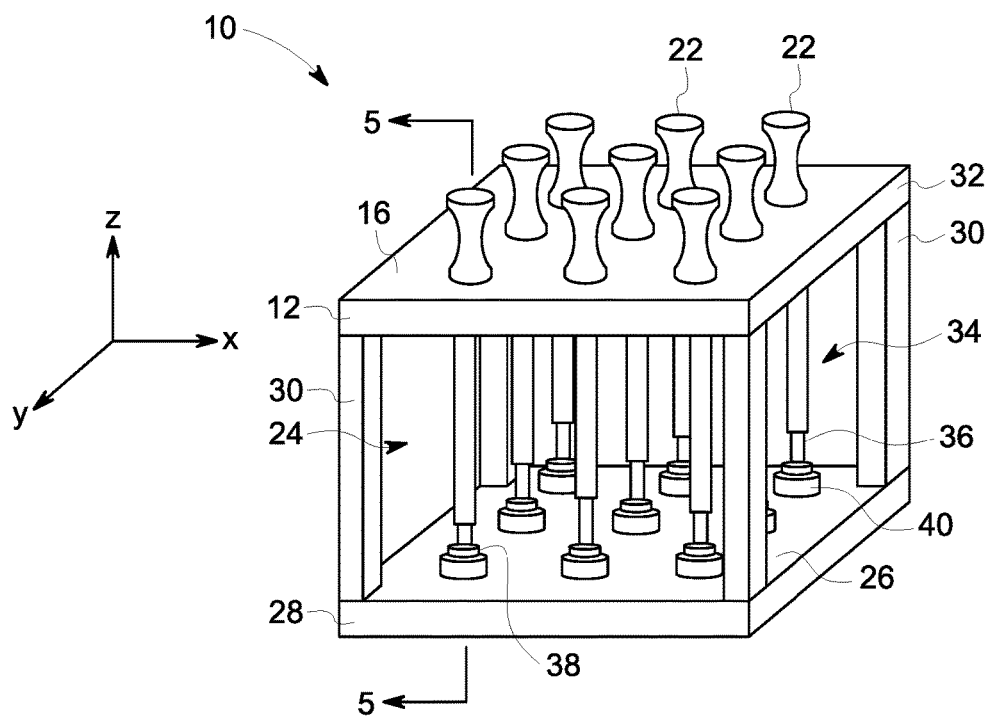
FIG. 1 is a schematic perspective of an embodiment of an apparatus for rapid screening of material properties in a plurality of additively manufactured test specimens, in accordance with one or more embodiments shown or described herein.

The detailed description explains embodiments of the disclosure, together with advantages and features, by way of example with reference to the drawings.

DETAILED DESCRIPTION

Reference now will be made in detail to embodiments of the disclosure, one or more examples of which are illustrated in the drawings. Each example is provided by way of explanation of the disclosure, not limitation of the disclosure. In fact, it will be apparent to those skilled in the art that various modifications and variations can be made in the present disclosure without departing from the scope or spirit of the disclosure. For instance, features illustrated or described as part of one embodiment can be used with another embodiment to yield a still further embodiment. Thus, it is intended that the present disclosure covers such modifications and variations as come within the scope of the appended claims and their equivalents.

Approximating language, as used herein throughout the specification and claims, may be applied to modify any quantitative representation that could permissibly vary without resulting in a change in the basic function to which it is related. Accordingly, a value modified by a term or terms, such as "about," is not limited to the precise value specified. In at least some instances, the approximating language may correspond to the precision of an instrument for measuring the value. Range limitations may be combined and/or interchanged, and such ranges are identified and include all the sub-ranges stated herein unless context or language indicates otherwise. Other than in the operating examples or where otherwise indicated, all numbers or expressions referring to quantities of ingredients, reaction conditions and the like, used in the specification and the claims, are to be understood as modified in all instances by the term "about."

"Optional" or "optionally" means that the subsequently described event or circumstance may or may not occur, or that the subsequently identified material may or may not be present, and that the description includes instances where the event or circumstance occurs or where the material is present, and instances where the event or circumstance does not occur or the material is not present.

As used herein, the terms "testing" and "screening" are used interchangeably to describe the procedure that is performed on the disclosed additively manufactured test specimens utilizing the apparatus disclosed herein.

As used herein, the terms "comprises", "comprising", "includes", "including", "has", "having", or any other variation thereof, are intended to cover a non-exclusive inclusion. For example, a process, method, article or apparatus that comprises a list of elements is not necessarily limited to only those elements, but may include other elements not expressly listed or inherent to such process, method, article, or apparatus.

As used herein, the singular forms "a", "an", and "the" include plural referents unless the context clearly dictates otherwise.

Embodiments of the present disclosure include an apparatus and method for rapid screening of material properties in a plurality of additively manufactured test specimens. The testing apparatus and method as disclosed herein provide for the high throughput screening and/or testing of multiple build strategies and/or multiple chemistries related to additively manufactured specimens disposed on a single build plate.

Referring now to the drawings, it is noted that like numerals refer to like elements throughout the several views and that the elements shown in the Figures are not drawn to scale and no dimensions should be inferred from relative sizes and distances illustrated in the Figures. Illustrated in FIG. 1 is an apparatus for rapid screening of material properties in a plurality of additively manufactured test specimens in accordance with an exemplary embodiment, as indicated generally at 10 in FIG. 1. In an embodiment, the apparatus 10 may also be referred to as a testing apparatus. The apparatus 10 includes a build plate 12, including a plurality of test specimens 22 disposed thereon. The plurality of test specimens 22 are, more specifically, additively manufactured test specimens 22. In an embodiment, the additively manufactured test specimens 22 may be geometrically the same. In the embodiment illustrated in FIG. 3, the additively manufactured test specimens 22 geometrically differ. The term "additively manufactured" should be understood to describe an additive manufacturing process that will be detailed more fully below. As will become more fully evident below, the term "additive manufacturing process" should be understood to describe the process by which components are constructed by forming successive layers of material one on top of another. The apparatus 10 further includes at least one actuator 34. In this particular embodiment, the apparatus includes a plurality of actuators 34, each translationally displacing at least one of the plurality of additively manufactured test specimens 22 along an axis "z", and perpendicular to the build plane 17 of the build plate 12 to test material properties of each of the plurality of additively manufactured test specimens 22. In this particular embodiment, the plurality of actuators 34 define an actuator array 24 disposed on an uppermost surface 26 of a support plate 28. A plurality of vertical support members 30 in cooperation with the support plate 28 and the build plate 12, define a frame-like structure 32 about the actuator array 24. The frame-like structure 32, and more particularly the support plate 28, provides structural support for the actuator array 24. In this particular embodiment, each of the plurality of actuators 34 is generally comprised of an actuator rod 36 and an actuating component 40. Each actuator 34 of the plurality being coupled thereto one of the plurality of additively manufactured test specimens 22 and a sensor component 38. In an embodiment, each actuator 34 of the plurality may simply be in contact with one of the plurality of additively manufactured test specimens 22 and provide a pushing action (upward force) and no pulling action. In an embodiment, the sensor component 38 may be a load cell. Each of the plurality of actuators 34 is configured for individual, translational displacement of the actuator rod 36, and thus a respective one of the plurality of additively manufactured test specimens 22, along an axis "z", generally perpendicular to the plane of the build plate 12. Displacement of the plurality of actuators 34, and more particularly the actuator rods 36, may be recorded electronically throughout the test. In a preferred embodiment, the sensor components 38 further measure and record a load applied to each of the plurality of additively manufactured test specimens 22. Tests may be run either in displacement control via the plurality of actuators 34, or load control via the plurality of sensors 38. Load vs. displacement data may be used to monitor the progression of monotonic and/or cyclic tests. Post-processing of such data can provide reliable measures of yield strength in monotonically tested specimens, and the evolution of cyclic stress/strain hysteresis in cyclically tested specimens, for example. Stress relaxation data may also be calculated from such data. Specimens may be screened on the basis of their performance against such property requirements.

Figure 2:
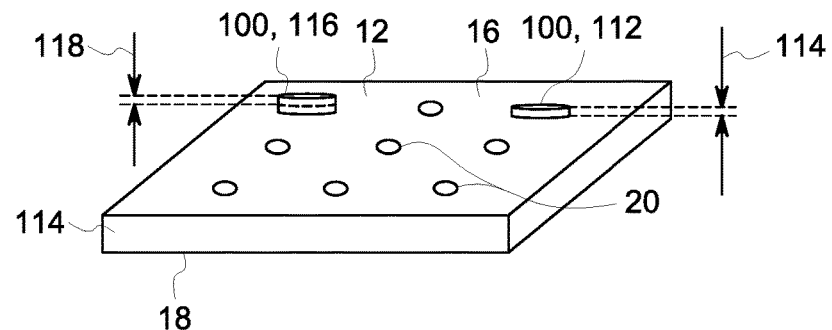
FIG. 2 is a schematic perspective of a build plate of FIG. 1, in accordance with one or more embodiments shown or described herein.
Figure 3:
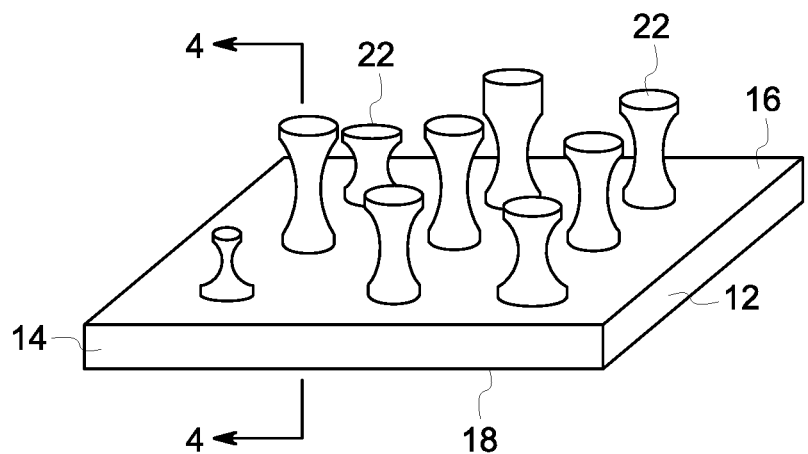
FIG. 3 is a schematic perspective of a build plate of FIG. 1, having a plurality of additively manufactured test specimens disposed thereon, in accordance with one or more embodiments shown or described herein.

Referring more specifically to FIGS. 2 and 3, in accordance with one aspect of the exemplary embodiment, illustrated is the build plate 12 including a body 14 having a first substantially planar surface 16 and an opposing, second substantially planar surface 18, and wherein the first substantially planar surface 16 defines a build plane 17. A plurality of openings 20 extend through first and second surfaces 16 and 18. Each of the plurality of openings 20 has disposed there over, and on the first surface 16 of the build plate 12, a respective one of the plurality of additively manufactured test specimens 22, as illustrated in FIG. 3. Each of the plurality of additively manufactured test specimens 22 is positioned in substantial alignment with one of the openings 20 formed therethrough the build plate 12.

Figure 4:
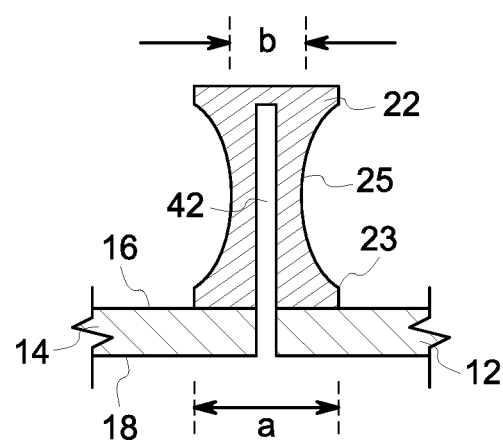
FIG. 4 is a cross-sectional view of a single additively manufactured test specimen disposed on the build plate, of FIG. 3 taken through line 4-4 of FIG. 3, in accordance with one or more embodiments shown or described herein.
Figure 5:
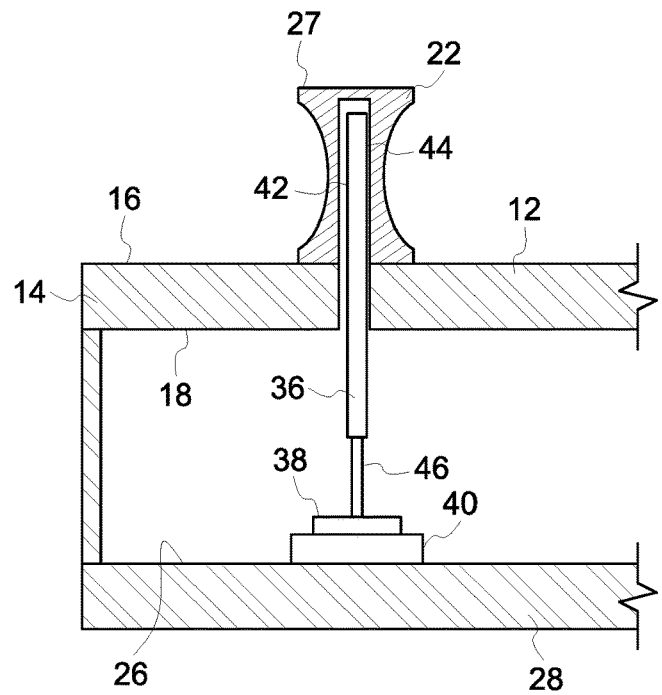
FIG. 5 is a cross-sectional view of a portion of the apparatus of FIG. 1 taken through line 5-5 of FIG. 1, in accordance with one or more embodiments shown or described herein.

As best illustrated in FIGS. 4 and 5, in which only one of the additively manufactured test specimens 22 is illustrated, each of the additively manufactured test specimens 22 is manufactured in such as manner to define therein a cavity 42. During assembly, as illustrated in FIG. 5, each of the actuator rods 36 is disposed relative to the respective opening 20 so as to protrude therethrough the build plate 12 and project beyond each of the first and second surface 16 and 18. A first end portion 44 of each of the actuator rods 36 projects beyond the first surface 16 and is positioned within the cavity 42 of a respective additively manufactured test specimen 22. A second end portion 46 of each of the actuator rods 36 is coupled to the sensor component 38 and the actuating component 40. In an embodiment, the plurality of openings 20 in the build plate 12 are configured to provide that the actuator rods 36 fit substantially tight within the openings 20 to maintain a desired positioning of the actuator rods 36, while allowing for individual, translational displacement of the actuator rod 36.

Referring again to FIG. 4, each of the plurality of additively manufactured test specimens 22 is coupled to the build plate 12 in a manner that provides for a cross-sectional area "a", at a base 23 of each specimen 22 disposed proximate the build plate 12, to be greater than a cross-sectional area "b" of a centralized portion 25 of the additively manufactured test specimens 22. In an embodiment cross-sectional area "a" is greater than cross-sectional area "b" by a ratio of approximately three to one. This ratio may be modified depending on the ratio of specimen strength to interfacial strength between the specimen and substrate. In an embodiment the base 23 of one or more of the additively manufactured test specimens 22 may include a greater cross-sectional area than a top 27 of the specimen, or otherwise modified, to provide improved attachment to the upper surface 16.

Figure 7:
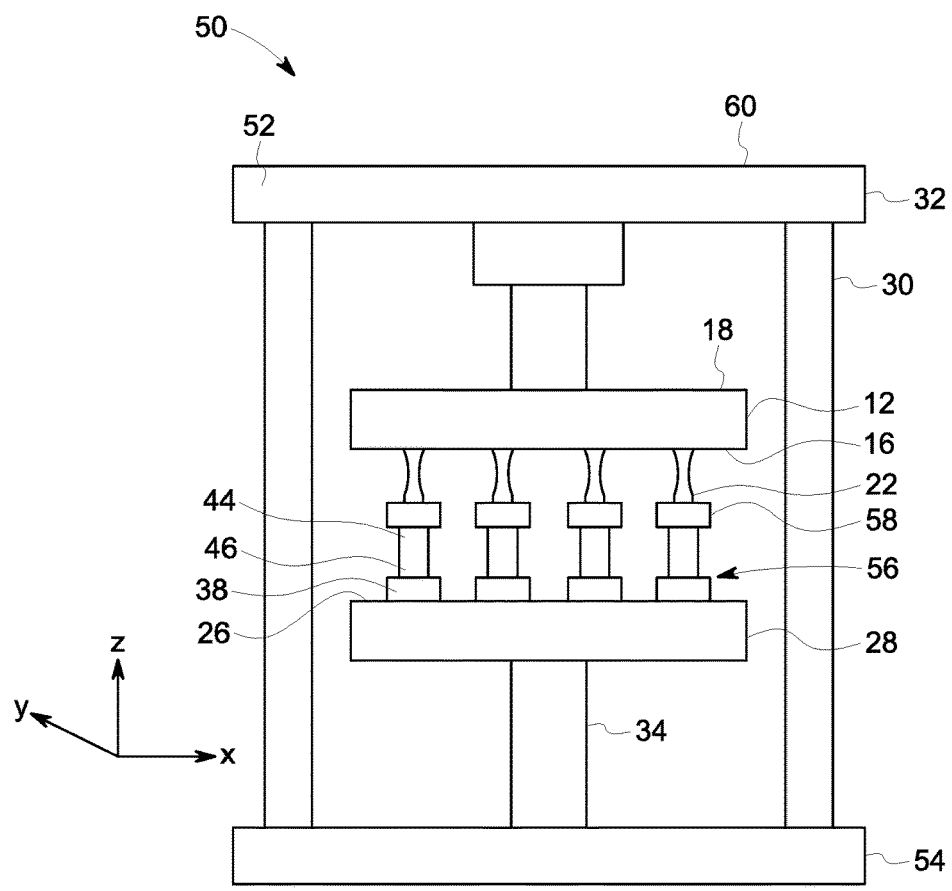
FIG. 7 is a schematic perspective of another embodiment of an apparatus for rapid screening of material properties in a plurality of additively manufactured test specimens, in accordance with one or more embodiments shown or described herein.
Figure 8:
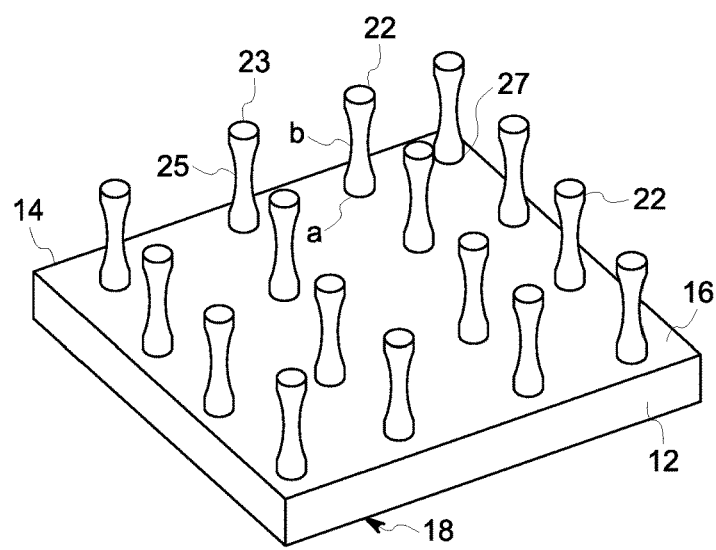
FIG. 8 is a schematic perspective of a build plate of FIG. 8 including a plurality of test specimens disposed thereon, in accordance with one or more embodiments shown or described herein.

Referring now to FIGS. 7 and 8, illustrated is another embodiment of an apparatus for rapid screening of material properties in a plurality of additively manufactured test specimens in accordance with an exemplary embodiment, as indicated generally at 50 in FIG. 7. It should again be noted that like numerals refer to like elements throughout the several views. In an embodiment, the apparatus 50 may also be referred to as a testing apparatus. The apparatus 50 includes a build plate 12, including a plurality of additively manufactured test specimens 22 disposed thereon. As previously noted, the term "additively manufactured" should be understood to describe an additive manufacturing process by which components are constructed by forming successive layers of material one on top of another, that will be detailed more fully below. The apparatus 50 further includes at least one actuator 34. In this particular embodiment, the apparatus includes a single actuator 34, translationally displacing the plurality of additively manufactured test specimens 22 along an axis "z", and perpendicular to the build plane 17 of the build plate 12, as illustrated in FIG. 8, to test material properties of each of the plurality of additively manufactured test specimens 22. In this particular embodiment, the apparatus 50 further comprises an array of pull-rods 56 coupled to an uppermost surface 26 of a support plate 28. The support plate 28 provides structural support for the array of pull-rods 56. Each of the pull-rods 56 is generally coupled to a respective one of the additively manufactured test specimens 22 by way of a grip 58 on a first end 44. A sensor component 38 is disposed proximate an opposed second end portion 46. In an embodiment, the sensor component 38 may be a load cell. Each of the grips 58 of the plurality being coupled thereto one of the plurality of additively manufactured test specimens 22.

In an embodiment, the apparatus 50 is installed in a servohydraulic test machine 60, schematically illustrated in FIG. 7 as including a plurality of vertical support members 30 in cooperation with an upper support, or crosshead 52 and a lower support 54 defining a frame-like structure 32 about the test assembly. The build plate 12 is coupled to the upper support 52 and may further include additional plates, flanges, spacers or the like to accomplish such coupling. The single actuator 34 is coupled to a lower surface 27 of the support plate 28. Upon movement (actuation) of the support plate 28, the array of pull-rods 56 are then actuated, or caused to simultaneously translationally displace each of the plurality of additively manufactured test specimens 22 along an axis "z", generally perpendicular to the build plane 17 of the build plate 12, to test material properties of each of the plurality of additively manufactured test specimens 22. In an embodiment, tests are run in displacement control, using the servohydraulic test machine 60 for control. Load vs. displacement data may then be used to monitor the progression of monotonic and/or cyclic tests. Post-processing of such data can provide reliable measures of yield strength in monotonically tested specimens, and the evolution of cyclic stress/strain hysteresis in cyclically tested specimens, for example. Stress relaxation data may also be calculated from such data. Cycles to failure may be used as a metric in cyclic tests as well. Each of the additively manufactured test specimens 22 may be screened on the basis of their performance against such property requirements.

Referring more specifically to FIG. 8, in accordance with one aspect of the exemplary embodiment, illustrated is the build plate 12 including a body 14 having a first substantially planar surface 16 and an opposing, second substantially planar surface 18, and wherein the first substantially planar surface 16 defines a build plane (FIG. 7). In contrast to the previous embodiment of FIGS. 1-6, in this particular embodiment the build plate 12 does not require a plurality of openings extending through first and second surfaces 16 and 18. In addition, in contrast to the embodiment of FIGS. 1-6 where the plurality of actuators 34 provided for individual translational displacement of the plurality of additively manufactured test specimens 22, in this particular embodiment, the single actuator 34 provides simultaneous, translational displacement of the plurality of additively manufactured test specimens 22.

Referring still to FIG. 8, each of the plurality of additively manufactured test specimens 22 is coupled to the build plate 12 in a manner that provides for a cross-sectional area "a", at a top 27 of each specimen 22 disposed proximate the build plate 12, to be greater than a cross-sectional area "b" of a centralized portion 25 of the additively manufactured test specimens 22. It should be noted that the build plate 22 as illustrated in FIG. 8, is inverted prior to coupling the grips 58 thereto in a manner illustrated in FIG. 7. As previously noted, in an embodiment cross-sectional area "a" is greater than cross-sectional area "b" by a ratio of approximately three to one. This ratio may be modified depending on the ratio of specimen strength to interfacial strength between the specimen and substrate. In an embodiment the top 27 of one or more of the additively manufactured test specimens 22 may include a greater cross-sectional area than a base 23 of the specimen that is coupled to the grip 58, or otherwise modified, to provide improved attachment to the upper surface 16.

Figure 9:
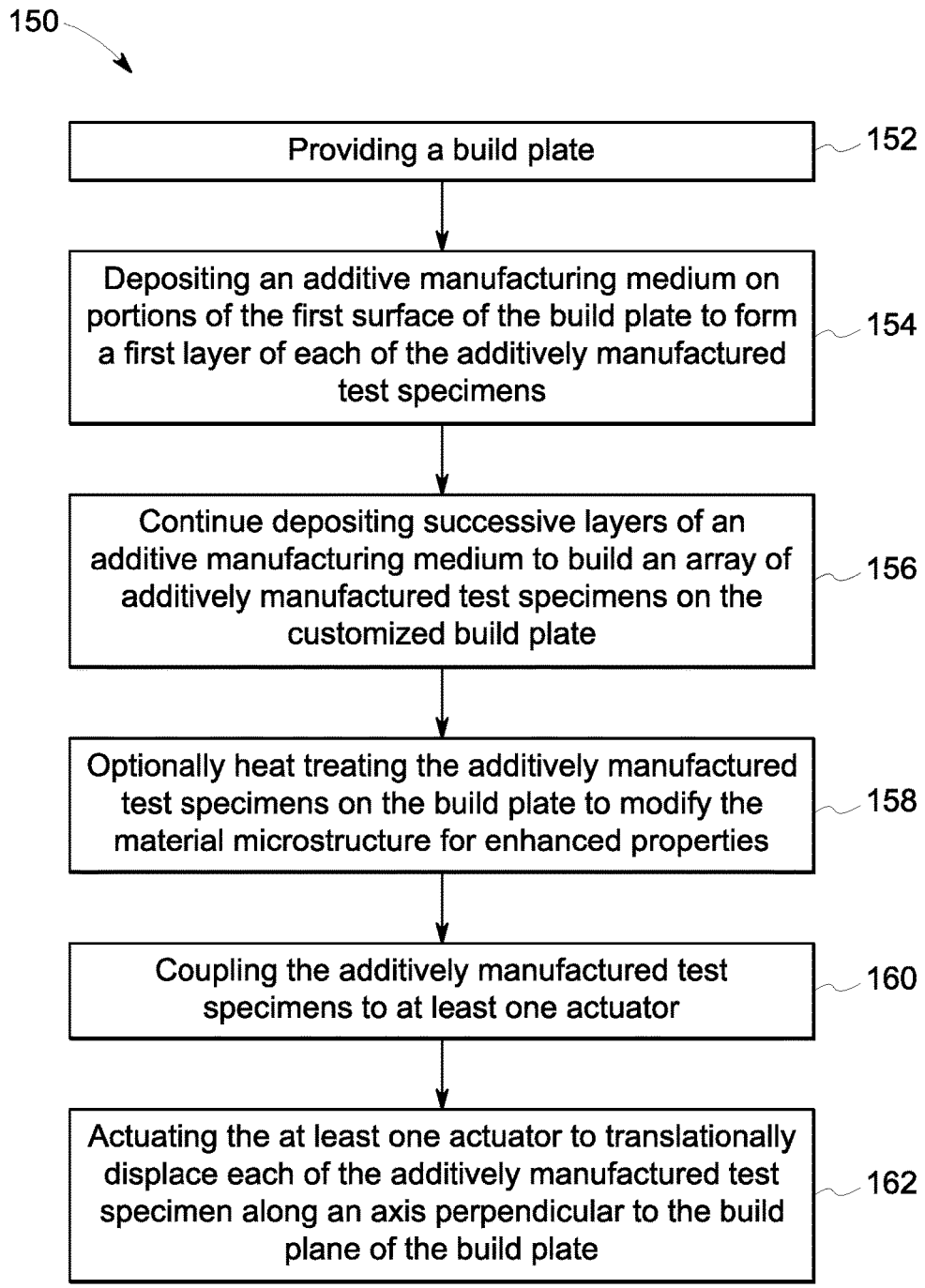
FIG. 9 is a flowchart illustrating a method of rapid screening of material properties in a plurality of additively manufactured test specimens, in accordance with one or more embodiments shown or described herein.

During a manufacture process 150, as illustrated in FIG. 9 with reference back to FIGS. 1-8, a build plate 12 is provided, in a step 152. In an embodiment, the build plate 12 may include the plurality of openings 20 formed therein as detailed in FIG. 2. Next in a processing chamber (not shown), portions of the first surface 16 of the build plate 12, are covered by an additive manufacturing medium 100 (FIG. 2), forming a first layer 112 (FIG. 2) of each of the additively manufactured test specimens 22 having a first height 114 (FIG. 2), in a step 154. The first layer of each additively manufactured test specimens 22 only adheres to, or bonds with, the first surface 16 of the build plate 12. Removable plugs (not shown) or the like, may be utilized to prevent additive manufacturing medium 100 from entering openings 20 in the build plate 12 if present, or to provide for the fabrication of the cavity 42 in each of the additively manufactured test specimens 22, if present. The first layer 112 of the additive manufacturing medium 100 is next deposited on the build surface 16 and exposed to heat, a laser, an electron beam or some other process and subsequently melted and solidified or otherwise sintered to form the first solid layer 112 in a designed shape. After deposition and consolidation of the first layer 112, a new layer is deposited, solidified, and/or fused to the previous layer until the component is formed. More particularly, additional additive manufacturing medium 100 is positioned upon the first layer 112 forming a second layer 116 (FIG. 2) having a second depth 118 (FIG. 2). Successive layers of additive manufacturing material 100 are added until each of the additively manufactured test specimens 22 are fully formed, in a step 156.

The plurality of additively manufactured test specimens 22, as best illustrated in FIGS. 3 and 8, are built using a range of machine parameters on the customized build plate 12. Upon completion of the additive manufacturing process to build the plurality of additively manufactured test specimens 22, the removable plugs may be withdrawn. Additive manufacturing medium 100 may be in the form of a metal powder or polymer and could include cobalt-chrome (Co—Cr). In accordance with an aspect of the exemplary embodiment, a selective laser melting process may be utilized to form the additively manufactured test specimens 22.

Subsequent to fabrication, the plurality of additively manufactured test specimens 22 may be heat treated on the build plate 12 to modify the material microstructure, in a step 158. More particularly, in an embodiment, subsequent to building the additively manufactured test specimens 22 on the build plate 12, the entire plate 12 and plurality of additively manufactured test specimens 22 may be submitted through one or more heat treatment cycles to produce desired material microstructures for enhanced properties.

The heat treatment process may be accomplished in a furnace (e.g. a standard furnace or a gradient furnace). In a gradient furnace, it would be possible to provide each of the plurality of additively manufactured test specimens 22 with a unique heat treatment such that the build processing and material post-processing space could be jointly investigated with one build. Thus, each of the plurality of additively manufactured test specimens 22 would have a completely unique processing history.

The build plate 12 and each of the additively manufactured test specimens 22 are then coupled to the at least one actuator 34 in a manner to one of individually, or simultaneously, translationally displace each of the plurality of additively manufactured test specimens 22 along an axis "z", and perpendicular to the build plane 17 of the build plate 12 to test material properties of each of the plurality of additively manufactured test specimens 22, in a step 160.

Subsequent to the coupling of the build plate 12 and the plurality of additively manufactured test specimens 22 to the at least one actuator 34, the additively manufactured test specimens 22 are next either independently, or simultaneously, tested by actuating the at least one actuator to translationally displace the additively manufactured test specimen 22, in a step 162. More particularly, in an embodiment the additively manufactured test specimens 22 are stressed independently by individually actuating each of a plurality of actuators 34 to translationally displace a respective one of the plurality of actuator rods 36 into the cavity 42 of a respective additively manufactured test specimen 22. In another embodiment, the additively manufactured test specimens 22 are stressed simultaneously by actuating the single actuator 34 to translationally displace the support plate 28 and thus the pull rod component 56 relative to each additively manufactured test specimens 22, along the axis "z" and generally perpendicular to the plane of the build plate 12.

Figure 6:
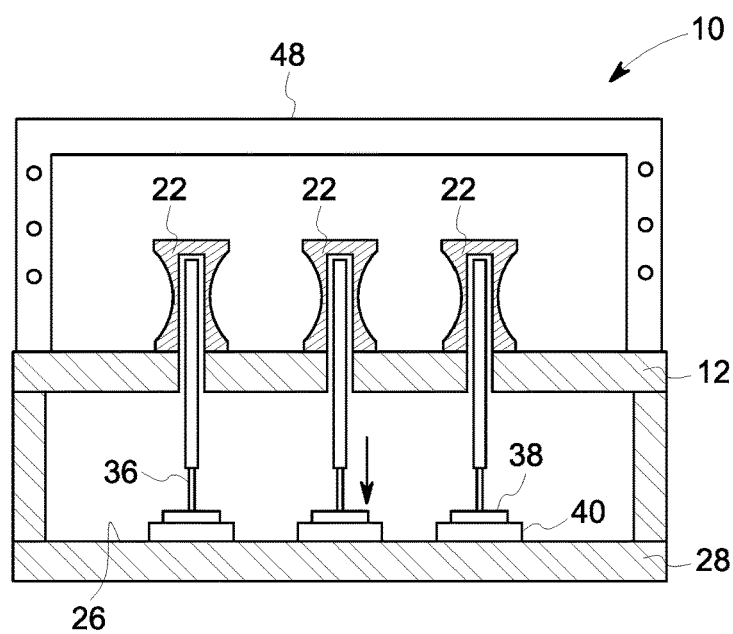
FIG. 6 is a cross-sectional view of the apparatus of FIG. 1 when placed in a furnace during testing, in accordance with one or more embodiments shown or described herein.

Several types of material tests may be performed during the rapid screening of material properties in a plurality of additively manufactured test specimens 22. In an embodiment, the at least one actuator 34 is cycled to test fatigue performance. In an embodiment, the at least one actuator 34 may provide translational displacement of the actuator rods 36 or pull-rod components 56 to a point of failure, so as to test tensile performance. In an embodiment, the at least one actuator 34 may provide translational displacement of the actuator rods 36 or pull rod components 56, with said being held in position, to measure stress relaxation. In an embodiment, the at least one actuator 34 may provide translational displacement of the actuator rods 36 or pull-rod components 56 to test both bulk and thin wall properties, depending on a wall thickness and geometry of the additively manufactured test specimen 22. In an embodiment, the at least one actuator 34 may provide translational displacement of the actuator rods 36 or pull-rod components 56 to provide compression testing of the additively manufactured test specimen 22. In an embodiment, the at least one actuator 34 may provide translational displacement of the actuator rods 36 or pull-rod components 56 to provide bend testing on the additively manufactured test specimen 22. In an embodiment, high temperature properties of the additively manufactured test specimen 22 are tested by positioning the build plate 12 and the additively manufactured test specimens 22 assembly in a custom furnace 48, as best illustrated in FIG. 6. In an embodiment, modifications to the system may be required to provide for such tests.

Accordingly, disclosed is an apparatus and method that addresses one of the main challenges in rapid qualification of additively manufactured (AM) materials: how to screen for material properties early in the process development. The disclosed apparatus includes a build plate 12 that may be customized for actuator placement if required, a plurality of additively manufactured test specimens 22 built onto the customized build plate 12, and at least one actuator 34 coupled to the plurality of additively manufactured test specimens 22. The apparatus enables materials property testing, including, but not limited to fatigue, tensile, bending, compression and stress relaxation. The apparatus may further provide for a customized furnace and/or chiller setup, such as illustrated in FIG. 6, to enable testing at a range of temperatures.

The apparatus and method for rapid screening of material properties in a plurality of additively manufactured test specimens as disclosed herein operates in the following manner. A plurality of additively manufactured test specimens 22 is built using a range of machine parameters on a customized build plate 12. The additively manufactured test specimens 22 may be heat treated on the customized build plate 12 to modify the material microstructure. The additively manufactured test specimens 22 can either all undergo the same thermal cycles or gradient heat treatments can be applied to test a range or responses at different locations on the build plate 12. Without removing the additively manufactured test specimens 22 from the build plate 12, the build plate 12 is coupled to at least one actuator 34 such that the plurality of additively manufactured test specimens 22 can be mechanically stressed. The build plate 12 and the additively manufactured test specimens 22 may be heated or cooled to assess properties at a range of temperatures. At a minimum, the apparatus provides for the following properties to be screened for thick (bulk) and thin walls: fatigue, tensile, bending, compression and stress relaxation.

The apparatus and method for rapid screening of material properties in a plurality of additively manufactured test specimens as disclosed herein incorporates material property screening into a standard methodology for processing optimization. It allows for rapid screening for preliminary build parameter optimization, prior to full testing in the traditional sequential manner. The apparatus and method as disclosed herein enables faster materials development for additive manufacturing in specific applications, providing materials property screening during the process optimization. Commercial advantages may be found due to the reduction in risk and time associated with failure to meet desired material properties after process development. The apparatus and method as disclosed herein may provide for a faster delivery of additively manufacture components.

It should be understood that the exemplary embodiments describe an apparatus and method for rapid screening of material properties in a plurality of additively manufactured test specimens. It should also be understood that while described as using a laser, other inputs could be used to act upon, and solidify, or otherwise consolidate the additive manufacturing material during the build process. Also, it should be understood that the relative size of the layers illustrated in FIG. 2, as well as the complete additively manufacturing test specimens, as illustrated in FIGS. 1, 3, and 5-8 are for exemplary purposes and to aid in a better understanding of the apparatus and method described in the application. In actuality, each layer may have a thickness of about 20 microns to about 100 microns, and each additively manufacturing test specimens may be comprised of any number of additively manufactured layers.

While the disclosure has been described in detail in connection with only a limited number of embodiments, it should be readily understood that the disclosure is not limited to such disclosed embodiments. Rather, the disclosure can be modified to incorporate any number of variations, alterations, substitutions or equivalent arrangements not heretofore described, but which are commensurate with the spirit and scope of the disclosure. Additionally, while various embodiments of the disclosure have been described, it is to be understood that aspects of the disclosure may include only some of the described embodiments. Accordingly, the disclosure is not to be seen as limited by the foregoing description, but is only limited by the scope of the appended claims.

What is claimed is:

1. An apparatus for rapid screening of material properties in a plurality of additively manufactured test specimens, the apparatus comprising:
    a build plate having a body, a first planar surface and an opposing second planar surface, the first planar surface defining a build plane;
    the plurality of additively manufactured test specimens disposed on and adhered to the first planar surface;
    at least one actuator, translationally displacing at least one of the plurality of additively manufactured test specimens along an axis to test material properties of at least one of the plurality of additively manufactured test specimens; and
    a plurality of sensors, wherein each of the plurality of sensors is coupled to a respective one of the plurality of additively manufactured test specimens.

2. The apparatus of claim 1, wherein the at least one actuator comprises a single actuator adapted to simultaneously, translationally displace the plurality of additively manufactured test specimens along an axis "z", and perpendicular to the build plane of the build plate, to test material properties of each of the plurality of additively manufactured test specimens.

3. The apparatus of claim 2, wherein the single actuator is coupled to a support plate having disposed thereon the plurality of sensors, each of the plurality of sensors coupled to a pull-rod and a respective one of the plurality of additively manufactured test specimens.

4. The apparatus of claim 3, wherein the apparatus is disposed in a servohydraulic test machine.

5. The apparatus of claim 1, wherein the at least one actuator comprises a plurality of actuators adapted to individually, translationally displace the plurality of additively manufactured test specimens along an axis "z", and perpendicular to the build plane of the build plate, to test material properties of each of the plurality of additively manufactured test specimens.

6. The apparatus of claim 5, wherein each of the plurality of actuators comprises an actuator rod one of coupled to or in contact with, a first end portion to a respective one of the plurality of additively manufactured test specimens and coupled at an opposed second end portion to a support plate having disposed thereon a plurality of sensors.

7. The apparatus of claim 6, wherein each actuator rod extends through an opening extending therethrough the first planar surface and the opposing second substantially planar surface of the build plate and into a cavity formed in a respective one of the plurality of additively manufactured test specimens.

8. The apparatus of claim 1, wherein each of the plurality of additively manufactured test specimens is coupled to the build plate in a manner that provides for a cross-sectional area "a" of each of the plurality of additively manufactured test specimens disposed proximate the build plate, to be greater than a cross-sectional area "b" of a centralized portion of the additively manufactured test specimens, and wherein the cross-sectional area "a" is greater than cross-sectional area "b".

9. The apparatus of claim 1, wherein the plurality of additively manufactured test specimens vary in geometry.

10. An apparatus for rapid screening of material properties in a plurality of additively manufactured test specimens, the apparatus comprising:
a build plate having a body, a first planar surface and an opposing planar second surface, the first planar surface defining a build plane;
the plurality of additively manufactured test specimens disposed on and adhered to the first planar surface, wherein the plurality of additively manufactured test specimens are formed through a selective laser melting process and wherein each of the plurality of additively manufactured test specimens is coupled to the build plate in a manner that provides for a cross-sectional area "a" of each of the plurality of additively manufactured test specimens disposed proximate the build plate, to be greater than a cross-sectional area "b" of a centralized portion of the additively manufactured test specimens, and wherein the cross-sectional area "a" is greater than cross-sectional area "b";
at least one actuator, each translationally displacing at least one of the plurality of additively manufactured test specimens along an axis "z", and perpendicular to the build plane of the build plate to test material properties of at least one of the plurality of additively manufactured test specimens; and
a plurality of sensors, wherein each of the plurality of sensors is coupled to a respective one of the plurality of additively manufactured test specimens.

11. The apparatus of claim 10, wherein the at least one actuator comprises a single actuator adapted to simultaneously, translationally displace the plurality of additively manufactured test specimens along an axis "z", and perpendicular to the build plane of the build plate, to test material properties of each of the plurality of additively manufactured test specimens.

12. The apparatus of claim 11, wherein the single actuator is coupled to a support plate and a plurality of sensors, and wherein each of the plurality of sensors is coupled to a pull-rod and a respective one of the plurality of additively manufactured test specimens, and wherein the apparatus is disposed in a servohydraulic test machine.

13. The apparatus of claim 10, wherein the at least one actuator comprises a plurality of actuators adapted to individually, translationally displace the plurality of additively manufactured test specimens along an axis "z", and perpendicular to the build plane of the build plate, to test material properties of each of the plurality of additively manufactured test specimens.

14. The apparatus of claim 13, wherein each of the plurality of actuators comprises an actuator rod one of coupled to, or in contact with, a first end portion to a respective one of the plurality of additively manufactured test specimens and at an opposed second end portion to a support plate having disposed thereon a plurality of sensors.

15. The apparatus of claim 14, wherein each actuator rod extends through an opening extending therethrough the first planar surface and the opposing second planar surface of the build plate and into a cavity formed in a respective one of the plurality of additively manufactured test specimens.

16. A method for rapid screening of material properties in a plurality of additively manufactured test specimens, the method comprising:
providing a build plate having a body, a first planar surface and an opposing planar second surface, the first planar surface defining a build plane;
covering portions of the first planar surface of the build plate with an additively manufactured medium in successive layers to form the plurality of additively manufactured test specimens, wherein the plurality of additively manufactured test specimens are adhered to the first planar surface;
coupling at least one actuator to a support plate having disposed thereon a plurality of sensors coupled to each of the plurality of additively manufactured test specimens; and
actuating the at least one actuator to translationally displace at least one of the plurality of additively manufactured test specimens along an axis to test material properties of each of the plurality of additively manufactured test specimens.

17. The method of claim 16, wherein the plurality of additively manufacture test specimens are heat treated on the build plate to modify a microstructure of each of the plurality of additively manufactured test specimens prior to actuating the at least one actuator and testing material properties of each of the plurality of additively manufactured test specimens.

18. The method of claim 16, wherein the step of actuating the at least one actuator includes simultaneously, translationally displacing a plurality of pull-rod components coupled to each of the plurality of additively manufactured test specimens along an axis "z", and perpendicular to the build plane of the build plate.

19. The method of claim 16, wherein the step of actuating the at least one actuator includes individually, translationally displacing a plurality of actuator rods coupled to each of the plurality of additively manufactured test specimens along an axis "z", and perpendicular to the build plane of the build plate.

20. The method of claim 16, wherein the step of actuating the at least one actuator includes cycling each of the at least one actuators to test fatigue performance of each of the plurality of additively manufactured test specimens.

21. The method of claim 16, wherein the step of actuating the at least one actuator includes exerting a force on the plurality of additively manufactured components to a point of failure to test tensile performance of each of the plurality of additively manufactured test specimens.

22. The method of claim 16, wherein the step of actuating the at least one actuator includes exerting a force on the plurality of additively manufactured components to measure stress relaxation of each of the plurality of additively manufactured test specimens.

23. The method of claim 16, wherein the step of actuating the at least one actuator includes exerting a force on the plurality of additively manufactured components to test bulk and thin wall properties of each of the plurality of additively manufactured test specimens.

24. The method of claim 16, wherein the step of actuating the at least one actuator includes exerting a force on the plurality of additively manufactured components to perform at least one of compression testing and bend testing of each of the plurality of additively manufactured test specimens.

25. The method of claim 16, further comprising positioning the build plate, having the plurality of additively manufactured test specimens formed thereon, in a furnace to test high temperature properties of each of the additively manufactured test specimens.

26. The method of claim 16, further comprising measuring a yield strength of the additively manufactured test specimens in a monotonic test.

27. The method of claim 16, further comprising measuring an evolution of cyclic stress/strain hysteresis and cycles to failure of the additively manufactured test specimens in a cyclical test.

* * * * *